United States Patent [19]

Yasuda et al.

[11] 4,451,399

[45] May 29, 1984

[54] IMIDAZOLECARBOXYLIC ACID DERIVATIVES

[75] Inventors: Naohiko Yasuda, Yokosuka; Masaru Okutsu, Yamato; Hisao Iwagami, Kawasaki; Teruaki Nakamiya, Tokyo; Ichiro Takase, Kawasaki, all of Japan

[73] Assignee: Ajinomoto Company, Inc., Tokyo, Japan

[21] Appl. No.: 445,663

[22] Filed: Nov. 30, 1982

Related U.S. Application Data

[63] Continuation of Ser. No. 170,928, Jul. 21, 1980, abandoned.

[30] Foreign Application Priority Data

Jul. 20, 1979 [JP] Japan .................................. 54-92940

[51] Int. Cl.³ .................. C07D 499/70; C07D 501/36
[52] U.S. Cl. .................................. 260/239.1; 424/246;
424/271; 544/22; 544/25; 544/27; 544/28

[58] Field of Search ................ 260/239.1; 544/22, 25, 544/27, 28

[56] References Cited

U.S. PATENT DOCUMENTS 4,147,693  4/1979  Konig et al. ........................ 424/246
4,217,450  8/1980  Yasuda et al. ........................ 544/25

FOREIGN PATENT DOCUMENTS 2248043  5/1975  France .
2394550  1/1979  France .

Primary Examiner—Natalie Trousof
Assistant Examiner—Vera C. Clarke
Attorney, Agent, or Firm—Oblon, Fisher, Spivak, McClelland & Maier

[57] ABSTRACT

The invention relates to imidazolecarboxylic acid derivatives of penicillins and cephalosporins, which are especially useful for the treatment of *Pseudomonas aeruginosa*-derived infections in humans and other animals.

10 Claims, No Drawings

IMIDAZOLECARBOXYLIC ACID DERIVATIVES

This is a continuation of application Ser. No. 170,928, filed July 21, 1980, now abandoned.

BACKGROUND OF THE INVENTION

1. Field of the Invention

The present invention relates to novel imidazolecarboxylic acid derivatives, which are useful as antibiotics, particularly as agents for treating human and other animal infectious diseases caused by bacteria, especially by *Pseudomonas aeruginosa*.

2. Brief Description of the Prior Art

It has been known that Penicillins and Cephalosporins having an amino group in the α-position shown by the general formula:

$$H_2N-CH-CO-NH-CH-CH-S$$
$$\underset{R}{|} \quad\quad\quad | \quad\quad | \quad |$$
$$\quad\quad\quad\quad\quad\quad\quad\quad C\!-\!\!-\!\!N\!-\!Y$$
$$\quad\quad\quad\quad\quad\quad\quad\quad \|$$
$$\quad\quad\quad\quad\quad\quad\quad\quad O$$

wherein R is selected from the group consisting of hydrogen, alkyl, aralkyl, aryl and hetero ring containing, and Y is an organic compound residue having one of the following formulas:

$$\underset{-\!\!C\!-\!COOH}{\overset{\diagdown C(CH_3)_2}{|}} \quad\text{and}\quad \underset{-\!C}{\overset{-CH_2\diagdown}{\underset{|}{\overset{\diagup}{C}\!\!-\!CH_2\!-\!Z}}}$$
$$\quad H \quad\quad\quad\quad\quad\quad\quad COOH$$

wherein the carbon bound to the —COOH group combines with the nitrogen atom, and the other carbon atom connects with the sulfur atom, and Z is selected from the group consisting of hydrogen, acyloxy, carbamoyloxy, heteroaromatic thio, quaternary ammonium; show antibacterial activity against not only gram positive bacteria but also gram negative bacteria. However, they show essentially no antibacterial activity against *Pseudomonas aeruginosa* which causes serious infectious diseases.

A need therefore continues to exist for penicillin and cephalosporin derivatives useful for the treatment of *Pseudomonas aeruginosa*-derived infections.

SUMMARY OF THE INVENTION

It is an object of the invention to provide an antibacterial agent useful against *Pseudomonas aeruginosa*.

This and other objects of the invention as will hereinafter become more readily apparent have been attained by providing novel imidazolecarboxylic acid derivatives of formula (1):

$$X_1\!\!-\!\!\underset{\underset{H}{N}}{\overset{N}{\diagup\!\!\diagdown}}\!\!\underset{}{\overset{X_2}{\diagdown\!\!\diagup}} \quad\quad (1)$$
$$\quad\quad\quad\quad CONH\!-\!CH\!-\!COA$$
$$\quad\quad\quad\quad\quad\quad\quad\quad | $$
$$\quad\quad\quad\quad\quad\quad\quad\quad R$$

wherein $X_1$ is selected from the group consisting of hydrogen; halogen; hydroxyl; alkyl-, aralkyl- and aryloxy; mercapto; alkyl-, aralkyl- and aryl-thio; alkyl-, aralkyl- and aryl-sulfonyl or sulfinyl; amino; mono- or di-alkyl-, aralkyl- or -aryl-amino; acylamino; sulfonyl; nitro; alkyl; aralkyl; aryl, and hetero ring-containing group.

$X_2$ is selected from the group consisting of hydrogen; halogen; nitro; amino; acylamino; alkyl- (such as methyl-, ethyl-, propyl- and butyl-), aralkyl- (such as benzyl-) and aryl- (such as phenyl-) oxycarbonyl; mono-or di-alkyl-, -aralkyl-, -aryl-carbomoyl; alkyl; aralkyl; aryl; and hetero ring-containing group.

R is selected from the group consisting of hydrogen; alkyl; aralkyl; aryl and hetero ring-containing group, and A is an organic compound residue having the following formula (2):

$$-NH\!-\!CH\!-\!CH\!-\!S \quad\quad (2)$$
$$\quad\quad\quad | \quad\quad | \quad |$$
$$\quad\quad\quad C\!-\!\!-\!\!N\!-\!Y$$
$$\quad\quad\quad \|$$
$$\quad\quad\quad O$$

wherein Y is an organic compound residue having one of the following formulas (3) and (4):

$$\underset{-\!\!C\!-\!COOH}{\overset{-C(CH_3)_2}{|}} \quad\text{and}\quad \underset{-\!C}{\overset{-CH_2\diagdown}{\underset{|}{\overset{\diagup}{C}\!\!-\!CH_2\!-\!Z}}}$$
$$\quad H \quad\quad\quad\quad\quad\quad\quad COOH$$
$$\quad(3) \quad\quad\quad\quad\quad\quad\quad\quad (4)$$

wherein the carbon atom which combines with the carboxyl group, combines with the nitrogen atom in Y, and z is selected from the group consisting of hydrogen, acyloxy (such as acetoxy), carbomoyloxy, heteroaromatic thio such as 5-(1-methyltetrazolyl) thio, 5-[1-(2-sulfoethyl)tetrazolyl] thio and 2-(1,3,4-thiadiazolyl) thio, quaternary ammonium such as pyridinium, quinolinium or picolinium, unsubstituted or substituted with a group such as 2-sulfoethyl and carboxymethyl.

DESCRIPTION OF THE PREFERRED EMBODIMENTS

Any of the alkyl, aralkyl and aryl, and heteroring-containing groups, has a carbon number in the range from 1 to 10, and may or may not be substituted.

The amino acid which forms the rest of the imidazolecarboxylic acid derivative of the present invention, which is derived from residue involving R in formula (1) described above, is, for example, phenylglycine or 4-hydroxyphenylglycine. Such amino acid is in the L-, D- or DL-form. In many cases, the D-form is suitable in view of antibacterial activity. In the derivatives of the formulae (2), (3), (4) described above, the hydrogen atom of carboxyl group of the Y shown therein may be replaced by a group, for example, a metal atom such as sodium, potassium, calcium, and aluminum, and tertiary ammonium such as triethylammonium, procaine, dibenzylammonium, N-benzyl-β-phenethylammonium and an amino acid such as L-lysine. The aforementioned salts, are thus included in the imidazolecarboxylic acid derivative. Of course, in such case, pharmaceutically acceptable, non-toxic replacement groups are employed.

The imidazolecarboxylic acid derivatives of the present invention have effective antibacterial activity against not only gram positive and gram negative bacteria but also against *Pseudomonas aeruginosa*. They therefore have a very broadspectrum antibacterial activity, and are very useful compounds as antibiotics or intermediates therefor.

The compounds of the present invention can be prepared by condensing α-amino-Penicillins or Cephalosporins of the following formula (5):

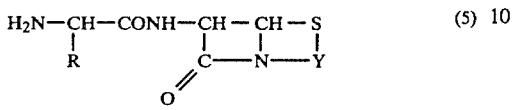

with a reactive derivative of an imidazolecarboxylic acid of the following formula (6):

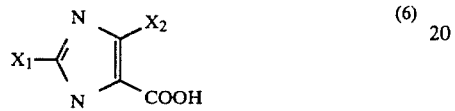

In the above formulas, $X_1$, $X_2$, R and Y have the same meanings and described previously.

Examples of suitable reactive derivatives of said imidazolecarboxylic acid, are acid halide derivatives, mixed acid anhydrides, active amides and active esters. Particularly, reactive derivatives having the following formula (7):

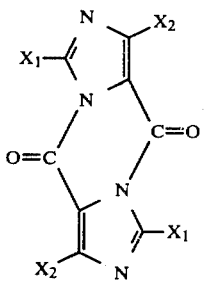

are frequently employed.

These derivatives can be prepared by reacting an imidazolecarboxylic acid derivatives (formula 8)

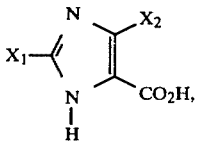

with a halogenating agent, such as thionyl chloride or phosphorus pentachloride.

Preferably, when $X_2$ represents an ester group of the formula, —$COOR_2$ wherein $R_2$ represents alkyl, aralkyl, aryl group, and heteroring-containing group, such derivative can be prepared by the following reaction scheme:

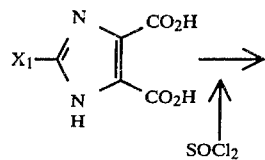

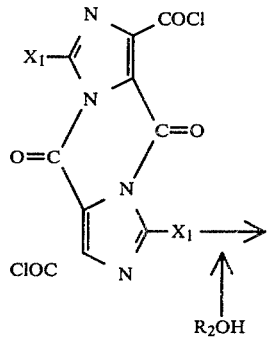

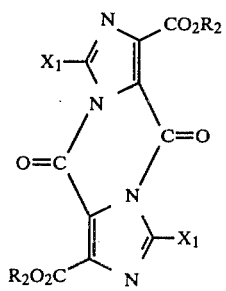

The reaction of the reactive derivative of the imidazolecarboxylic acid (as described above), with α-aminopenicillins or α-aminocephalosporins, is carried out under basic conditions such as in the presence of alkali metal bicarbonate, alkali metal carbonate, trialkylamine, or pyridine. A solvent such as water, acetone, dioxane, acetonitrile, chloroform, methylenechloride, tetrahydrofuran (THF), or dimethyl formamide (DMF) can be employed in the reaction. Hydrophilic organic solvents can be used in the mixture with water. The reaction may be carried out preferably at room temperature or less.

2 Moles of α-aminopenicillins or α-aminocephalosporins are used for each mole of the reactive derivative (5,10-dioxo-5,10-dihydrodimmidazo[1,5a:1',5'd] pyrazine-1,6-dicarboxylic acid ester).

In the reaction with the reactive derivative, α-aminopenicillins or α-aminocephalosporins shown by general formula (5) as described above, can be used wherein the carboxyl group in Y is esterified. For example, t-butyl esters, benzyl esters, silyl esters, trichloroethyl esters, diphenylmethyl esters, and the like, can be used in the reaction. Subsequent to the reaction, the ester groups can be removed to regenerate the free carboxylic acid groups.

The object compounds, modified α-aminocephalosporins shown by the formula (1) described above, wherein A has a cephalosporin backbone and Z is a heteroaromatic thio group or tertiary ammonium group, can be obtained by synthesizing the corresponding cephalosporins wherein Z is an acetoxy group, and then replacing the acetoxy group by the heteroaromatic thio group or quaternary ammonium group by conventional methods.

As regards the object compounds, modified α-aminocephalosporins shown by the formula (1) described above, wherein $X_2$ is a group such as amino and acylamino, the compound wherein X is an amino group can be obtained by synthesizing the corresponding cephalosporins wherein $X_2$ is a nitro group, and then changing the nitro group to the amino group by catalytic reduction reaction. By acylating the thus obtained compound wherein $X_2$ is an amino group with an acid halide or the like, the object compound wherein $X_2$ is an acylamino group can be obtained.

The reaction products of the modification reaction can be isolated in pure form by known procedures, for example by extraction, column chromatography, recrystallization and the like.

The thus obtained imidazolecarboxylic acid derivative is transformed to non-toxic salts thereof such as alkali metal salts, ammonium salt, with an organic base. These salts are desirable for preparations, since they are soluble in water.

Having now generally described this invention, the same will be better understood by reference to the following specific examples, which are included for purposes of illustration only and are not intended to be limiting thereof.

EXAMPLE 1

4-nitroimidazole-5-carboxylic acid (1.57 g, 10 mM) was suspended in dry benzene (20 ml), and DMF (3 drops) and then thionyl chloride (4 ml) were added thereto. The obtained mixture was refluxed at a temperature of 80° C. while stirring for 3 hours. After completion of the reaction, the reaction mixture was concentrated to yield solid material. The remaining material was washed with a mixture of benzene (10 ml) and petroleum ether (10 ml), then obtained by filtration, and dried to give the reactive derivative, 1,6-dinitro-5,10-dioxo-5,10-dihydrodiimidazo (1,5a, 1',5'd) pyrazine (1.3 g, 4.7 mM). Yield: 94%

I. R. spectrum (Nujol): 1755 cm$^{-1}$, 1550 cm$^{-1}$, 1285 cm$^{-1}$, 1230 cm$^{-1}$.

On the other hand, anhydrous D(-)-α-aminobenzyl-penicillin (2.8 g, 8 mM) was suspended in dichloromethane (30 ml). Triethylamine (4.5 ml) was added to this mixture and a homogeneous solution was obtained. The reactive derivative which had been previously synthesized, was added to this solution while stirring under cooling. The mixture was stirred under cooling for two hours, and then was stirred overnight at room temperature. Insoluble material was removed by filtration from the reaction solution and the obtained solution was concentrated under reduced pressure at 30° C. or lower to yield a solid material. The obtained solid material was dissolved in water (50 ml) and then ethyl acetate (50 ml) was added thereto to make two phases. The ethyl acetate phase was removed and to the obtained aqueous phase was added ethyl acetate (80 ml) and then 6% aqeuous HCl solution, while stirring to adjust the aqueous phase to pH 1.5. The precipitated insoluble material was removed by filtration and a solution having two phases was obtained. From the aqueous phase, organic material was extracted with ethyl acetate (70 ml), once more. All the obtained ethyl acetate phases were combined and dried over anhydrous magnesium sulfate. The ethyl acetate solution was concentrated at 30° C. or lower and ether was added to the obtained solid material to produce a powder. The powder was collected by filtration and dried to give the desired product, D-α-(4-nitroimidazole-5-carboxyamide) benzyl penicillin (2.6 g, yield: 67%).

The obtained product was dissolved in a mixture (30ml) of methanol and ethyl acetate (v/v=1/1) and to the solution was added 2-ethylhexane carboxylic acid sodium salt n-butanol solution (2 M/l) (3.3 ml). The mixture was stirred for 10 minutes, and ether (70 ml) was added to this mixture dropwise to precipitate the solid material. This material was cooled in the refrigerator, and the obtained solid material was obtained by filtration and dried to give the desired product, D-α-(4-nitroimidazole-5-carboxyamide) benzyl-penicillin sodium salt (3.0 g).

I.R. spectrum (Nujol): $\nu_{co}$(β-lactam)=1770 cm$^{-1}$.

EXAMPLES 2–9

The products shown by the following formula (9) were produced in the same manner as described in Example 1. The results are listed in Table 1.

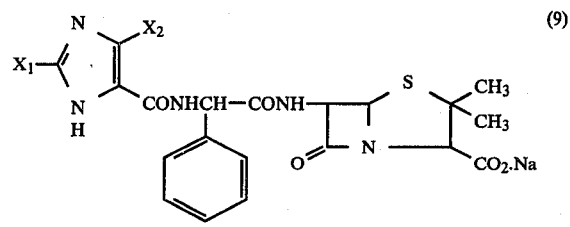

(9)

TABLE 1

| Example No. | Products of the Present Invention | | I.R. Spectrum $co^{(\beta\text{-}lactom)}_{(Nujol)}$ | Yield |
|---|---|---|---|---|
| | $X_1$ | $X_2$ | | |
| 2 | —H | —H | 1780 cm$^{-1}$ | 11 |
| 3 | —H | —Cl | 1780 | 23 |
| 4 | —H | —NHSO$_2$CH$_3$ | 1780 | 19 |
| 5 | —H | —CH$_3$ | 1780 | 31 |
| 6 | —H | —NHCOCH$_3$ | 1770 | 56 |
| 7 | —SCH$_2$—⟨⟩ | —COOC$_2$H$_5$ | 1780 | 62 |
| 8 | —SH | —CH$_3$ | 1775 | 43 |
| 9 | —OH | —H | 1770 | 28 |

EXAMPLE 10

30% Pd—BaCO$_3$ (4.8 g) was suspended in water (60 ml) and was activated by stirring the mixture under 30 atmospheric pressure of H$_2$ in an autoclave for 1 hour. To this mixture D-α-(4-nitroimidazole-5-carboxyamide) benzylpenicillin sodium salt (1.5 g, 3 mM) was obtained in Example 1 in water (60 ml), solution was added. Reduction reaction was carried out by stirring the thus obtained mixture under 30 atmospheric pressure of H$_2$ at room temperature for 1 hour. After completion of the reaction, the catalyst was obtained by filtration, and the pH of the aqueous solution was adjusted to 7 and then thus obtained mixture was washed with ethyl acetate (200 ml). To the aqueous phase was added ethyl acetate (200 ml) and then was added 6% aqueous HCl solution while stirring to adjust the aqueous phase to pH 1.5.

The ethyl acetate phase was separated and then organic material was extracted from the aqueous phase, with ethyl acetate (200 ml). All the obtained ethyl acetate phases were combined, washed with water and dried over anhydrous magnesium sulfate.

The ethyl acetate solution was concentrated at 30° C. or less and ether was added to the thus obtained residue to produce a powder. The thus obtained powder was collected by filtration and dried to give the desired product, D-α-(4-aminoimidazole-5-carboxyamide) benzylpenicillin (1.0 g, yield: 73% ).

I.R. spectrum (Nujol): $\nu_{co}(\beta$-lactam$)=1775$ cm$^{-1}$.

EXAMPLE 11

7-β-[D(-)-β-aninophenylacetoamide] cephalosporanic acid (1.8 g, 4.5 mM) was suspended in dichloromethane (20 ml), and triethylamine (2.5 ml) was added to this mixture to give a homogeneous solution. 1.6-dinitro-5,10-dioxo-5,10-dihydrodiimidazo [1.5a, 1',5'd] pyrazine (0.8 g, 2.9 mM) as produced in the same manner as in Example 1, was added to this solution while stirring under cooling. Hereinafter in the same manner as in Example 1, the desired product, 7-β-[D(-)-α-(4-nitroimida zole-5-carboxyamide)-phenylacetomide]-cephalosporanic acid sodium salt (1.3 g, yield: 53%).

I.R. spectrum (Nujol): $\nu_{co}(\beta$-lactam$)=1785$ cm$^{-1}$, $\nu_{co}(-\text{OCOCH}_3)=1745$ cm$^{-1}$.

N.M.R. spectrum (Solvent: D$_2$O): δ2.06 (S, 3H) (—OCOCH$_3$), 3.28 (m, 2H) (>CH$_2$, 2-position), 4.95 (d, 1H) (—H, 6-position), 5.60 (S, 1H)

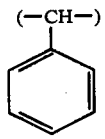

(—CH—)

5.66 (d, 1H) (—H, 7-position), 7.33 (b, S, 5H)

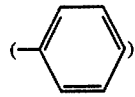

7.82 (S, 1H) (—H, 2-position of imidazole ring).

EXAMPLE 12

Imidazoledicarboxylic acid (7.8 g, 0.05 M) was suspended dry benzene (100 ml), and thereto DMF (4 ml) and then thionyl chloride (30 ml) were added. The thus obtained mixture was refluxed at a temperature of 85° C. while stirring for six hours. After completion of the reaction, the reaction solution was concentrated to give solid material. To the solid material dry benzene (50 ml) was added and the thus obtained mixture was concentrated to give a solid material, once more. To the remaining material benzene (50 ml) was added and the mixture was stirred at room temperature for 30 minutes. The insoluble material was obtained by filtration, washed with benzene, and dried under reduced pressure to give the desired product, 5,10-dioxo-5,10-dihydrodiimidazo [1,5a, 1',5'd] pyrazine-1,6-dicarboxylic acid dichloride (7.0 g, yield: 89%).

The thus obtained acid chloride derivative (7.0 g) was suspended in ethanol (150 ml) and the thus obtained mixture was stirred at room temperature overnight. The insoluble solid material was obtained by filtration, washed with ethanol and then ether, and dried under reduced pressure to give 5,10-dioxo-5,10-dihydrodiimidazo [1,5a, 1',5'd] pyrazine-1,6-dicarboxylic acid diethyl ester (7.0 g, yield: 94%).

I.R. specturm (Nujol): 1760 cm$^{-1}$, 1745 cm$^{-1}$, 1725 cm$^{-1}$, 1570 cm$^{-1}$, 1255 cm$^{-1}$, 1190 cm$^{-1}$, 1140 cm$^{-1}$, 1010 cm$^{-1}$, 925 cm$^{-1}$, 743 cm$^{-1}$.

Elemental analysis: Found: C 49.60%, H 3.61%, N 16.52%. Calcd. as C$_{14}$H$_{12}$N$_4$O$_6$: C 50.60%, H 3.64%, N 16.86%.

On the other hand, 7-β-[D(-)-α-aminophenylacetoamide] cephalosporanic acid (3.2 g, 8 mM) was suspended in dichloromethane (50 ml), and to this mixture triethylamine (3 ml) was added to give a homogeneous solution. To this solution, 5,10-dioxo-5,10-dihydrodiimidazo [1,5a, 1',5'd] pyrazine-1,6-dicarboxylic acid diethyl ester (1.3 g, 4 mM) was added while stirring under cooling. The mixture was stirred at room temperature overnigth. The thus obtained mixture was concentrated to give solid material. To this material water (30 ml) was added and stirred to give a homogeneous solution. The solution was adjusted to pH 7.5 by adding 6% aqueous HCl solution, stirred for 10 minutes, and then washed with ethyl acetate (50 ml). The aqueous phase was adjusted to pH 2 by adding 6% aqueous HCl solution, and then stirred for 20 minutes. The precipitated crystal was obtained by filtration, washed with water, and then dried under reduced pressure at 40° C. The thus obtained solid material was suspended in a mixture (300 ml) of ethyl acetate and ethanol (volume ratio: 1/1). The mixture was stirred at 40° C. for 20 minutes. An insoluble material was obtained and then an organic phase was concentrated under reduced pressure to volume of 50 ml. To this mixture ether (500 ml) was added and the thus obtained mixture was stood in a refrigerator overnight.

The precipitated crystal was obtained by filtration, washed with petroleum ether, and dried to give the desired object product, 7-β-[D(-)-α-(4-ethoxycarbonylimidazole-5-carboxyamide)-phenylacetoamide] cephalosporanic acid (3.4 g, yield: 75%).

I.R. spectrum (Nujol): $\nu_{co}(\beta$-lactam$)=1775$ cm$^{-1}$, $\nu_{co}(-\text{CO}_2\text{Et})=1730$ cm$^{-1}$.

EXAMPLE 13

Anhydrous D(—)-α-aminobenzylpenicillin (2.8 g, 8 mM) was reacted with 5,10-dioxo-5,10-dihydrodiimidazo [1,5a, 1',5'd] pyrazine-1,6-dicarboxylic acid diethyl ester (1.3 g, 4 mM) to give D-α-(4-ethoxycarbonylimidazole-5-carboxyamide) benzylpenicillin (3.0 g, yield: 73%) in the same manner as in Example 12.

I.R. spectrum (Nujol): $\nu_{co}(\beta$-lactam$)=1770$ cm$^{-1}$, $\nu_{co}(-\text{CO}_2\text{Et})=1730$ cm$^{-1}$.

N.M.R. spectrum (d$_6$-DMSO): δ1.33 (t, 3H) (—COOCH$_2$CH$_3$), 1.43 (s, 3H)

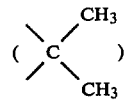

1.57 (s, 3H) 4.20 (s, 1H) (—H, 3-position), 4.37 (q, 2H) (—COOCH$_2$—CH$_3$), 5.30 5.70 (m, 2H) (—H, 5-position; —H, 6-position), 5.98 (d, 1H)

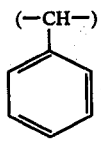

7.40 (m, 5H)

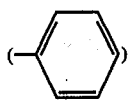

7.83 (s, 1H) (—H, 2-position of imidazole).

EXAMPLE 14

5,10-dioxo-5,10-dihydrodiimidazo [1,5a, 1',5'd] pyrazine-1,6-dicarboxylic acid dichloride (7.0 g) obtained in Example 12, was suspended in water (150 ml) and the thus obtained mixture was stirred at room temperature overnight. An insoluble solid material was obtained by filtration, washed with water, a little THF, and ether successively, and dried under reduced pressure to give the desired product, 5,10-dioxo-5,10-dihydroimidazo [1,5a, 1',5'd] pyrazine-1,6-dicarboxylic acid 2 hydrate (7.0 g, yield: 100%). Melting point: 284° C. (dec.).

I.R. spectrum: 3500 cm$^{-1}$, 1750 cm$^{-1}$, 1710 cm$^{-1}$, 1255 cm$^{-1}$, 930 cm$^{-1}$.

Elemental analysis: Found: C 38.65%, H 2.40%, N 18.02%. Calcd. for $C_{10}H_4N_4O_6 \cdot 2H_2O$: C 38.47%, H 2.58%, N 17.95%.

Isobutylamine (6.6 g, 90 mM) was dissolved in dichloromethane (200 ml), and thereto triethylamine (22 ml) and then the above mentioned 5,10-dioxo-5,10-dihydrodiimidazo [1,5a, 1',5'd] pyrazine-1,6-dicarboxylic acid 2 hydrate (9.4 g, 30 mM) were added. The thus obtained mixture was reacted while stirring and being heated at 40° C. for 5 hours. An insoluble material was removed by filtration, and the remaining filtrate was concentrated. The remaining residue was dissolved in water (150 ml) to give pH of the aqueous solution 10. From the solution two times extractions with ethyl acetate (150 ml) were carried out, and then the aqueous phase was adjusted to pH 2 with 2 N—HCl. The thus obtained mixture was stood in a refrigerator overnight. The precipitated material was obtained by filtration and dried under reduced pressure and heating. The thus obtained material was dissolved and heated at 50° C. in THF (300 ml) to dissolved the material. An insoluble material was removed by filtration. The obtained filtrate was concentrated and thereto ether was added to produce crystal. The thus obtained mixture was cooled overnight. The precipitated crystal was obtained by filtration, washed with petroleum ether, and dried under reduced pressure to give 4-isobutylcarbamoylimidazole-5-carboxylic acid (9.2 g, yield: 73%).

N.M.R. spectrum (d$_6$-DMSO): δ0.90 (d, 6H) (—CH(CH$_3$)$_2$), 1.98 (m, 1H) (—CH$_2$—C$\underline{H}$), 3.20 (dd, 2H) (—C$\underline{H}_2$—CH), 8.08 (s, 1H) (—H, 2-position of imidazole), 9.33 (t, 1H) (—CON$\underline{H}$CH$_2$—).

The thus obtained 4-isobutylcarbamoylimidazole-5-carboxylic acid (2.1 g, 10 mM) was suspended in dry benzene (30 ml), and thereto DMF (5 drops) and then thionyl chloride (6 ml) were added. The thus obtained mixture was refluxed at 80° C. while stirring for 4 hours. After completion of the reaction the reaction mixture was concentrated under reduced pressure to give a solid material.

To the thus obtained material dry benzene (30 ml) was added, and the thus obtained solution was concentrated to give a solid material, once more, and therefore 1,6-isobutylcarbamoyl-5,10-dioxo-5,10-dihydrodiimidazo [1,5a, 1',5'd] pyrazine was obtained.

On the other hand, 7-β-[D(-)-α-aminophenylacetoamide] cephalosporanic acid (4.0 g, 10 mM) was suspended in dichloromethane (75 ml), and thereto triethylamine (4.5 ml) was added to give a homogeneous solution.

The thus obtained solution was added to the suspending solution of the reactive derivative which had been previously prepared in dichloromethane (30 ml) while stirring and being cooled. The mixture was stirred under cooling for 2 hours and then stirred at room temperature overnight.

From the reaction solution an insoluble material was removed by filtration and the filtrate was concentrated under reduced pressure at 30° C. or less to give a solid material. The thus obtained solid material was dissolved in water (50 ml), and ethyl acetate (50 ml) was added thereto to make two phases.

The ethyl acetate phase was removed and to the obtained aqueous phase ethyl acetate (80 ml) was added and then 6% aqueous HCl solution was added while stirring to adjust the aqueous phase to pH 1.5. The precipitated insoluble material was removed by filtration and a solution having two phases was obtained from the aqueous phase, organic material was extracted with ethyl acetate (80 ml), once more. All the obtained ethyl acetate phase were combined and dried over anhydrous magnesium sulfate. The ethyl acetate solution was concentrated at 30° C. or lower and to the thus obtained residue ether was added to produce a powder. The thus obtained mixture was stood in a refrigerator overnight. The powder was collected by filtration and dried to give the desired product, 7-β-[D(-)-α-(4-isobutylcarbamoylimidazole-5-carboxyamide)-phenylacetoamide] cephalosporanic acid (2.2 g, yield: 37%).

I.R. spectrum (Nujol): $v_{co}$(β-lactam)=1780 cm$^{-1}$, $v_{co}$(—OCOCH$_3$)=1730 cm$^{-1}$.

N.M.R. spectrum (d$_6$-DMSO): δ0.90 (d, 6H) (—CH(C$\underline{H}_3$)$_2$), 2.00 (s, 3H) (—OCO.C$\underline{H}_3$), whose signal overlaps one of "—C$\underline{H}$(CH$_3$)$_2$—", 3.10 (m, 2H) (—C$\underline{H}_2$—CH<), 3.45 (m, 2H) (>CH$_2$, 2-position), 4.80 (q, 2H) (>CH$_2$, 3-position), 5.00 (d, 1H) (—H, 6-position), 5.75 (m, 2H)

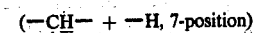

7.30 (b, s, 5H)

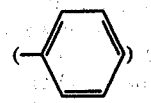

7.82 (s, 1H) (—H, 2-position of imidazole).

EXAMPLE 15

5,10-dioxo-5,10-dihydrodiimidazo [1,5a,1',5'd] pyrazine-1,6-dicarboxylic acid.2 hydrate was reacted with morpholine in the same manner as in Example 14 to give 4-morpholinocarbonylimidazole-5-carboxylic acid (Yield: 16%).

N.M.R. spectrum (d6-DMSO): δ3.70 (b,s, 8H)

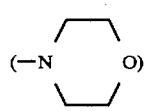

8.00 (s, 1H) (—H, 2-position of imidazole).

The thus obtained product was reacted with 7-β-[D(-)-α-aminophenylacetoamide] cephalosporanic acid in the same manner as Example 14 to give the desired product, 7-β-[D(-)-α-(4-morpholinocarbonylimidazole-5-carboxyamide)-phenylacetoamide] cephalosporanic acid (Yield: 21%).

EXAMPLE 16

4-Diethylcarbamoylimidazole-5-carboxylic acid was obtained (yield: 12%) by reacting 5,10-dioxo-5,10-dihydrodiimidazo [1,5,1',5'd] pyrazine-1,6-dicarboxylic acid.2 hydrate with diethyl amine in the same manner as in Example 14.

N.M.R. spectrum (d6-DMSO): δ1.22 (t, 6H) (—CH2CH3), 3.90 (q, 4H) (—CH2CJ3), 7.90 (s, 1H) (—H, 2-position of imidazole).

This product was reacted with 7-β-[D(-)-α-aminophenylacetoamide] cephalosporanic acid in the same manner as in Example 14 to give the desired product, 7-β-[D(-)-α-(4-diethylcarbamoylimidazole-5-carboxyamide)-phenylacetoamide] cephalosporanic acid & yield: 28%).

EXAMPLE 17

7-β-[D(-)-α-(4-ethoxycarbonylimidazole-5-carboxyamide)-phenylacetoamide] cephalosporanic acid (1.7 g, 3 mM) as produced in Example 21 and 4-pyridine ethane sulfonic acid (1.1 g, 6 mM) were suspended in water (15 ml), and thereto 2 N—NaOH aqueous solution was added dropwise while stirring pH of the solution was adjusted to 7, and therefore a homogeneous solution was obtained. Sodium iodide (12 g) were added thereto, and the thus obtained mixture was reacted while stirring at 70° C. for 2 hours. After completion of the reaction, the reaction solution was treated with Amberlite XAD-2 produced by Rhom and Haas Co., Ltd. (700 ml) for absorption and excess sodium iodide and 4-pyridine ethane sulfonic acid were eluted with water. By elution with a mixture of water and methanol (1:1), the desired product was eluted. Fractions of the desired product were collected, and therefrom methanol was removed under reduced pressure. By freeze-drying the remaining solution, the desired product, 7-β-[D-(-)-α-(4-ethoxycarbonylimidazole-5-carboxyamide)-phenylacetoamide]-3-(4-β-sulfoethylpyridinium)-methyl-3-cephem-4-carboxylic acid sodium salt was obtained (0.59 g, yield: 26%).

I.R. spectrum (Nujol): ν$_{co}$(β-lactam)=1760 cm$^{-1}$, ν$_{so2}$(—SO3H)=1210 cm$^{-1}$, 1040 cm$^{-1}$.

N.M.R. spectrum (D2O): δ1.33 (t, 3H) (—CO—OCH2C$\underline{H}$3), 3.20 (m, 2H) (>CH2, 2-position), 3.44 (s, 4H)

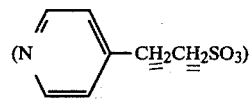

4.20 (t, 2H) (—C—O C$\underline{H}$2CH3), 5.05 (d, 1H) (—H, 6-position), 5.40 (m, 2H)

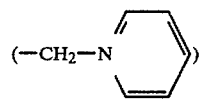

5.62 (s, 1H)

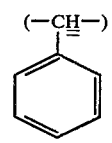

5.75 (d, 1H) (—H, 7-position, 7.40 (b,s, 5H)

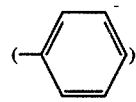

7.85 (s, 1H) (—H, 2-position of imidazole), 7.97 (d, 2H) (—H, 3 and 5-position of pyridine ring), 8.84 (d, 2H) (—H, 2 and 6-position of pyridine ring).

EXAMPLE 18

7-β-[D(-)-α-(4-ethoxycarbonylimidazole-5-carboxyamide)-phenylacetoamide] cephelosporanic acid (1.5 g, 2.6 mM) as produced in Example 12 and 1-methyl-5-mercaptotetrazole (0.33 g, 2.9 mM) were suspended in phosphate buffer solution (pH 6.4) (25 ml) and then 2 N—NaOH aqueous solution was added dropwise to adjust the solution to pH 6.4, and therefore a homogeneous solution was obtained. This solution was reacted while stirring at 60° C. for 24 hours. In such reaction, after 5 hours' reaction the solution was adjusted to pH 6.4 with 2 N—NaOH aqueous solution. After completion of the reaction water (45 ml) was further added to the reaction mixture and then the solution was adjusted to pH 7 with 2 N—NaOH aqueous solution.

An insoluble material was removed by filtration, and the thus obtained filtrate was washed with ethyl acetate (60 ml). To the aqueous solution ethyl acetate (100 ml) was added and then 6% aqueous HCl solution while stirring to adjust the aqueous phase to pH 2.0. An insoluble material was removed by filtration and a solution having two phases was obtained. From the aqueous phase, organic material was extracted with ethyl acetate (100 ml), once more. All the obtained ethyl acetate phases were combined, washed with water, and then dried over anhydrous magnesium sulfate.

The ethyl acetate solution as concentrated and to thus obtained solid material ether was added to produce a powder. The thus obtained mixture was cooled in a refrigerator, and then the thus produced powder was obtained by filtration and dried to give the desired product. 7-β-[D(-)-α-(4-ethoxycarbonylimidazole-5-carboxyamide)-phenylacetoamide]-3-(1-methyl-1H-tetrazole- 5-yl)thiomethyl-3-cephem-4-carboxylic acid (0.7 g, yield: 47%).

I.R. spectrum (Nujol): $\nu_{co}(\beta\text{-lactam})=1770$ cm$^{-1}$.

N.M.R. spectrum (d$_6$-DMSO): $\delta$1.35 (t, 3H) (—CO-OCH$_2$CH$_3$), 3.60 (m, 2H) (>CH$_2$, 2-position), 3.93 (s, 3H) (—CH$_3$ in tetrazole, 4.30 (m, 4H) (—CO.OCH$_2$CH$_3$+—CH$_2$—S—, 3-position), 4.96 (d, 1H) (—H, 6-position, 5.50 5.90 (m, 2H)

(—H, 7-position + —CH—)
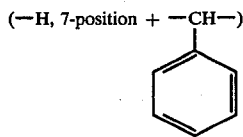

7.30 (m, 5H)

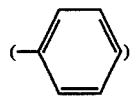

7.83 (s, 1H) (—H, 2-position of imidazole).

EXAMPLES 19–24

The compounds shown by the following formula (10):

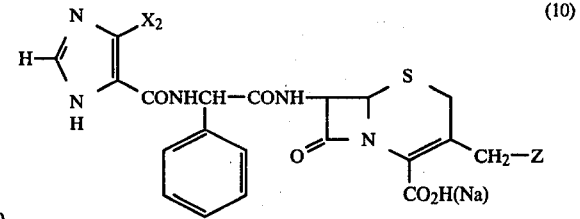

were produced in the same manner as in Examples 17 and 18, by using the compounds produced in Examples 14–16 as starting materials. The results are shown in Table 2.

TABLE 2

| Example No. | Compounds of the Present Invention X$_2$ | Z | I.R. Spectrum (Nujol) (cm$^{-1}$) | Yield % |
|---|---|---|---|---|
| 19 | —CONHCH$_2$CH(CH$_3$)$_2$ | +—N⟨pyridine⟩—CH$_2$CH$_2$SO$_3^-$ | 1760 1640 1215 1040 | 23% |
| 20 | " | —S—C(=N-N=N-N(CH$_3$))— (methyltetrazolylthio) | 1760 | 53% |
| 21 | —CON⟨morpholine⟩O | +—N⟨pyridine⟩—CH$_2$CH$_2$SO$_3^-$ | 1760 1640 1210 1040 | 18% |
| 22 | " | —S—C(=N-N=N-N(CH$_3$))— | 1765 | 34% |
| 23 | —CON(C$_2$H$_5$)$_2$ | +—N⟨pyridine⟩—CH$_2$CH$_2$SO$_3^-$ | 1760 1640 1210 1040 | 21% |
| 24 | " | —S—C(=N-N=N-N(CH$_3$))— | 1760 | 37% |

EXAMPLES 25

5,10-dioxo-5,10-dihydrodiimidazo [1,5a,1',5'd] pyrazine-1,6-dicarboxylic acid diethyl ester (1.3 g, 4 mM) as produced in Example 12 was reacted with anhydrous D(-)-α-amino-4-hydroxybenzylpenicillin (2.9 g, 8 mM) in the same manner as in Example 13 to give the desired product, D-α-(4-ethoxy-carbonylimidazole-5-carboxyamide)-4-hydroxybenzylpenicillin (2.1 g, yield: 50%).

$\nu_{c=o}(\beta\text{-lactam})=1770$ cm$^{-1}$, $\nu_{c=o}(—CO_2Et)=1730$ cm$^{-1}$.

EXAMPLES 26–30

5,10-dioxo-5,10-dihydrodiimidazo [1,5a,1',5'd] pyrazine-1,6-dicarboxylic acid dichloride was reacted with an alcohol shown by the general formula: R'OH, in the same manner as in Example 12, to produce the compounds shown by the formula (11):

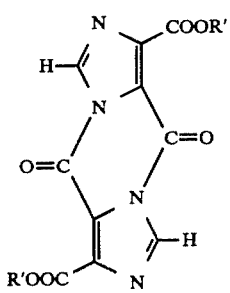

Results are shown in Table 3.

TABLE 3

| Example No. | Compound R' | N.M.R. spectrum (d$_6$-DMSO) | Yield (%) |
|---|---|---|---|
| 26 | —CH$_3$ | δ: 3.93 (6H,S), 8.97 (2H,S) | 93.8 |
| 27 | —CH(CH$_3$)$_2$ | δ: 1.37 (12H,d), 5.23 (2H, Sept), 8.93 (2H,S) | 84.9 |
| 28 | —CH$_2$CH$_2$CH$_2$CH$_3$ | δ: 0.93(6H,t), 1.53(4H,m), 1.70(4H,m), 4.33(4H,t), 8.93(2H,s) | 49.8 |
| 29 | —CH$_2$CH(CH$_3$)$_2$ | δ: 1.00(12H,d), 2.07(2H,non) 4.13(4H,d), 8.97(2H,S) | 76.6 |
| 30 | —CH$_2$—C$_6$H$_5$ | δ: 5.43(4H,S), 7.47(10H,m), 8.93(2H,S) | 69.9 |

The thus obtained compound was reacted with anhydrous D(-)-α-aminobenzylpenicillin in the same manners described in Examples 12 and 13, to produce the compounds shown by the following formula (12):

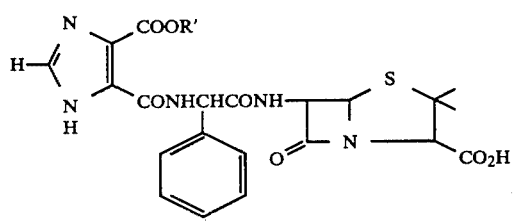

TABLE 4

| Example No. | Compound R' | N.M.R. spectrum (d$_6$-DMSO) | Yield (%) |
|---|---|---|---|
| 26 | —CH$_3$ | δ: 1.43(3H,s), 1.57(3H,S), 3.90(3H,S), 4.22(1H,S), 5.30-5.80 (2H), 6.00(1H), 7.10-7.70(5H), 7.87(1H,S) | 25.0 |

TABLE 4-continued

| Example No. | Compound R' | N.M.R. spectrum (d$_6$-DMSO) | Yield (%) |
|---|---|---|---|
| 27 | —CH(CH$_3$)$_2$ | δ: 1.33(6H,d),1.42(3H,S), 1.57(3H,S),4.20(1H,S), 5.20(1H,m),5.27-5.80(2H), 5.97(1H),7.10-7.70(5H), 7.83(1H,S) | 17.4 |
| 28 | —CH$_2$CH$_2$CH$_2$CH$_3$ | δ: 0.93(3H,t),1.27-1.93(4H,m) 1.43(3H,S),1.57(3H,S), 4.20(1H,S),4.33(2H,t), 5.33-5.67(2H),6.00(1H), 7.07-7.73(5H),7.83(1H,S) | 29.0 |
| 29 | —CH$_2$CH(CH$_3$)$_2$ | δ: 1.03(6H,d),1.43(3H,S), 1.57(3H,S),1.70-2.33(1H), 4.13(2H,d),4.20(1H,S), 5.33-5.67(2H),6.00(1H), 7.10-7.77(5H),7.87(1H,S) | 23.0 |
| 30 | —CH$_2$—C$_6$H$_5$ | δ: 1.43(3H,S),1.57(3H,S), 4.20(1H,S),5.27-5.80(2H), 5.40(2H,S),6.00(1H), 7.07-7.73(10H),7.87(1H,S) | 19.4 |

BIOLOGICAL TESTS

The imidazolecarboxylic acid derivatives of the present invention have a good antibacterial activity with a wide spectrum of activity, particularly against *Pseudomonas, aeruginosa.*

Antibacterial activity was determined with regards to the compounds produced in the examples described above. Some of Comparative Minimum Inhibitory Concentrations (MIC) (the minimum concentration of the compound in micrograms per milliliter required to inhibit the growth of the test organism in a culture) obtained using *Pseudomonas aeruginosa* AJ 2116 as the test organism, are presented in Table 5.

TABLE 5

| Sample Example No. | MIC (μg/ml) |
|---|---|
| 1 | 12.5 |
| 3 | 25 |
| 8 | 25 |
| 13 | 25 |
| Carbenicillin | 100 |
| Ampicillin | More than 500 |

The imidazolecarboxylic acid derivatives of the present invention have a good oral absorption, as is evident from Table 6.

TABLE 6

| | Concentration in Blood (μg/ml) Mouse (ICR 5W ♂) | | |
|---|---|---|---|
| | Oral Administration: 50 mg/kg Time (minutes) | | |
| Sample | 30 | 60 | 90 |
| Compound produced in Example 13 | 340 | 97 | 40 |
| Ampicillin | 81 | 306 | 41 |

As is evident from the results, it can be concluded that the imidazolecarboxylic acid derivatives of the present invention have good antibacterial activity and oral absorption, and therefore, can be practically used as medicines for human beings and other animals, particularly for oral administration.

The compounds of this invention can be administered by any means that affects palliating conditions of bacterial infection, especially *Pseudomonas aeruginosa* infection in warm blooded animals. For example, administration can be parenterally, subcutaneously, intravenously, intramuscularly or intraperitoneally. Alternatively, or concurrently, administration can be the oral route. The dosage administered will be dependent upon the age, health, and weight of the recipient, kind of concurrent treatment if any, frequency of treatment, and the nature of the effect desired. Generally, daily dosage of active ingredient compounds will be from about 0.1 mg to 100 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 95% by weight.

Having now specifically described this invention, it will be apparent to one of skill in the art that the same is subject to many obvious modifications and variations without affecting or changing the scope thereof.

What is claimed as new and intended to be secured by Letters Patent of the United States is:

1. A compound having the formula (I):

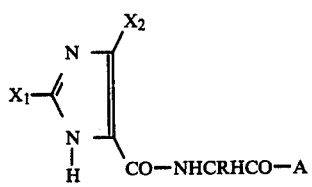

wherein
$X_1$ is selected from the group consisting of hydrogen, halogen, hydroxyl, alkyloxy, aralkyloxy, aryloxy, mercapto, alkylthio, aralkylthio, arylthio, alkylsulfonyl, aralkylsulfonyl, arylsulfonyl, alkylsulfinyl, aralkylsulfinyl, arylsulfinyl, amino, mono- or di-alkylamino, -aralkylamino or -arylamino, acylamino, sulfonyl, nitro, alkyl, aralkyl and aryl;
$X_2$ is selected from the group consisting of hydrogen, halogen, nitro, amino, acylamino, mono- or di-alkylcarbamoyl, -aralkylcarbamoyl or -arylcarbamoyl, alkyl, aralkyl, aryl, and morpholino-4-carbonyl;
R is selected from the group consisting of hydrogen, alkyl, aralkyl, and aryl; and
A is an organic residue of the formula (II):

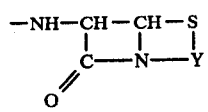

wherein Y is an organic residue having one of the following formulas (III) or (IV):

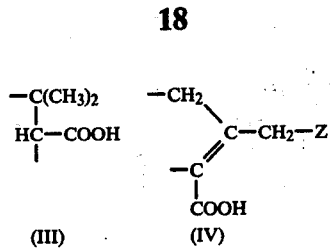

wherein
the carbon atom which combines with the COOH combines with nitrogen atom in Y, and
Z is selected from the group consisting of hydrogen, acyloxy, carbamoyloxy, 5-(1-methyltetrazolyl)-thio, 5-(1-(2-sulfoethyl)tetrazolyl)thio, 2-(1,3,4-thiadiazolyl)thio, and quaternary ammonium which may be unsubstituted or substituted by sulfoethyl or carboxymethyl,
or a pharmaceutically acceptable salt thereof.

2. The compound of claim 1, wherein R is phenyl or 4-hydroxyphenyl.

3. The compound of claim 1, wherein the portion of formula (I) written as —NHCRHCO— represents the residue of a D-amino acid.

4. The compound of claim 1, wherein said compound is a salt.

5. The compound of claim 1, wherein $X_1$ is hydrogen and Y has the formula (III).

6. A compound having the formula (I):

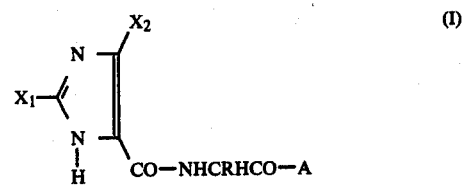

wherein
$X_1$ is selected from the group consisting of hydrogen, halogen, hydroxyl, alkyloxy, aralkyloxy, aryloxy, mercapto, alkylthio, aralkylthio, arylthio, alkylsulfonyl, aralkylsulfonyl, arylsulfonyl, alkylsulfinyl, aralkylsulfinyl, arylsulfinyl, amino, mono- or di-alkylamino, -aralkylamino or -arylamino, acylamino, sulfonyl, nitro, alkyl, aralkyl and aryl;
$X_2$ is selected from the group consisting of hydrogen, halogen, nitro, amino, acylamino, aralkyloxycarbonyl, aryloxycarbonyl, mono- or di-alkylcarbamoyl, -aralkylcarbamoyl or -arylcarbamoyl, alkyl, aralkyl, aryl, and morpholino-4-carbonyl;
R is selected from the group consisting of hydrogen, alkyl, aralkyl, and aryl; and
A is an organic residue of the formula (II):

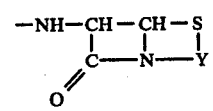

wherein
Y is an organic residue having one of the following formulas (III) or (IV):

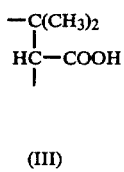
(III)

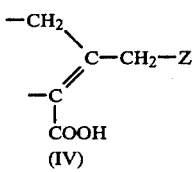
(IV)

wherein
the carbon atom which combines with the COOH combines with nitrogen atom in Y, and Z is selected from the group consisting of hydrogen, acyloxy, carbamoyloxy, 5-(1-methyltetrazolyl)thio, 5(1-(2-sulfoethyl)tetrazolyl)thio, 2-(1,3,4-thiadiazolyl)thio, and quaternary ammonium which may be unsubstituted or substituted by sulfoethyl or carboxymethyl, or a pharmaceutically acceptable salt thereof.

7. The compound of claim 6, wherein R is phenyl or 4-hydroxyphenyl.

8. The compound of claim 6, wherein the portion of said formula written as —NHCRHCO— represents the residue of a D-amino acid.

9. The compound of claim 6, wherein said compound is a salt.

10. The compound of claim 6, wherein $X_1$ is hydrogen and Y has the formula (III).

* * * * *